US006818172B2

(12) United States Patent
King et al.

(10) Patent No.: US 6,818,172 B2
(45) Date of Patent: Nov. 16, 2004

(54) ORIENTED, CROSS-LINKED UHMWPE MOLDING FOR ORTHOPAEDIC APPLICATIONS

(75) Inventors: Richard King, Warsaw, IN (US); Donald E. McNulty, Warsaw, IN (US); Todd S. Smith, Fort Wayne, IN (US); Robert Richard, Wrentham, MA (US)

(73) Assignee: DePuy Products, Inc., Warsaw, IN (US)

( * ) Notice: Subject to any disclaimer, the term of this patent is extended or adjusted under 35 U.S.C. 154(b) by 198 days.

(21) Appl. No.: 09/961,842

(22) Filed: Sep. 24, 2001

(65) Prior Publication Data

US 2002/0125614 A1 Sep. 12, 2002

Related U.S. Application Data

(60) Provisional application No. 60/236,958, filed on Sep. 29, 2000.

(51) Int. Cl.[7] .......................... B29C 35/08; B29C 43/02; B29C 43/52; B29C 71/00
(52) U.S. Cl. ........................ 264/479; 264/237; 264/294; 264/320; 264/322; 264/488
(58) Field of Search ................................ 264/237, 294, 264/320, 322, 479, 488

(56) References Cited

U.S. PATENT DOCUMENTS

| 2,948,666 | A | 11/1960 | Lawton |
|---|---|---|---|
| 3,297,641 | A | 1/1967 | Werber et al. |
| 3,352,818 | A | 11/1967 | Meyer et al. |
| 3,646,155 | A | 2/1972 | Scott |
| 3,671,477 | A | 6/1972 | Nesbitt |
| 3,758,273 | A | 9/1973 | Johnston et al. |
| 3,944,536 | A | 3/1976 | Lupton et al. |
| 4,055,862 | A | 11/1977 | Farling |
| 4,138,382 | A | 2/1979 | Polmanteer |
| 4,281,420 | A | 8/1981 | Raab |
| 4,366,618 | A | 1/1983 | Lakes |
| 4,390,666 | A | 6/1983 | Moriguchi |
| 4,483,333 | A | 11/1984 | Wartman |
| 4,518,552 | A | 5/1985 | Matsuo et al. |
| 4,539,374 | A | 9/1985 | Fenton et al. |
| 4,582,656 | A | 4/1986 | Hoffmann |
| 4,586,995 | A | 5/1986 | Randall et al. |
| 4,655,769 | A | 4/1987 | Zachariades |
| 4,668,527 | A | 5/1987 | Fujita et al. |
| 4,743,493 | A | 5/1988 | Sioshansi et al. |
| 4,747,990 | A | 5/1988 | Gaussens et al. |
| 4,816,517 | A | 3/1989 | Wilkus |
| 4,876,049 | A | 10/1989 | Aoyama et al. |
| 4,888,369 | A | 12/1989 | Moore, Jr. |
| 4,902,460 | A | 2/1990 | Yagi |
| 4,944,974 | A | 7/1990 | Zachariades |
| 5,014,494 | A | 5/1991 | George |
| 5,024,670 | A | 6/1991 | Smith et al. |
| 5,037,928 | A | 8/1991 | Li et al. |
| 5,130,376 | A | 7/1992 | Shih |
| 5,133,757 | A | 7/1992 | Sioshansi et al. |
| 5,137,688 | A | 8/1992 | DeRudder |
| 5,153,039 | A | 10/1992 | Porter et al. |
| 5,160,464 | A | 11/1992 | Ward et al. |
| 5,160,472 | A | 11/1992 | Zachariades |
| 5,180,394 | A | 1/1993 | Davidson |
| 5,192,323 | A | 3/1993 | Shetty et al. |
| 5,200,439 | A | 4/1993 | Asanuma |
| 5,210,130 | A | 5/1993 | Howard, Jr. |
| 5,236,563 | A | 8/1993 | Loh |
| 5,356,998 | A | 10/1994 | Hobes |
| 5,407,623 | A | 4/1995 | Zachariades et al. |
| 5,414,049 | A | 5/1995 | Sun et al. |
| 5,439,949 | A | 8/1995 | Lucas et al. |
| 5,449,745 | A | 9/1995 | Sun et al. |
| 5,466,530 | A | 11/1995 | England et al. |
| 5,478,906 | A | 12/1995 | Howard, Jr. |
| 5,480,683 | A | 1/1996 | Chabrol et al. |
| 5,508,319 | A | 4/1996 | DeNicola |
| 5,515,590 | A | 5/1996 | Pienkowski |
| 5,543,471 | A | 8/1996 | Sun et al. |

(List continued on next page.)

FOREIGN PATENT DOCUMENTS

| BE | 1001574 A | 12/1989 |
|---|---|---|
| EP | 0 169 259 A1 | 1/1985 |
| EP | 0 373 800 A1 | 6/1990 |
| EP | 0722973 A1 | 7/1996 |
| EP | 0729981 A1 | 9/1996 |
| EP | 0 737 481 A1 | 10/1996 |
| EP | 0 963 824 A2 | 12/1999 |
| EP | 0 963 824 A3 | 9/2001 |
| JP | 58-157830 A | 9/1983 |
| JP | 59 168 050 A | 9/1984 |
| JP | 62 243 634 A | 1/1987 |
| JP | 04 185651 A | 7/1992 |
| JP | 04-198242 A | 7/1992 |
| JP | 09 12 22 22 A | 5/1997 |
| WO | 93/10953 A1 | 10/1993 |
| WO | 95/21212 A1 | 8/1995 |
| WO | 96/09330 A1 | 3/1996 |
| WO | 97/29793 A1 | 8/1997 |
| WO | 98/01085 A1 | 1/1998 |
| WO | 98/14223 A1 | 4/1998 |

OTHER PUBLICATIONS

"Poly Two Carbon–Polyethylene Composite–A Carbon Fiber Reinforced Molded Ultra–High Molecular Weight Polyethylene", Technical Report, Zimmer (a Bristol–Myers Squibb Company), Warsaw (1977).

(List continued on next page.)

Primary Examiner—Leo B. Tentoni
(74) Attorney, Agent, or Firm—Barnes & Thornburg LLP

(57) ABSTRACT

A process for forming an oriented orthopaedic implant prosthesis bearing, net-shape bearing, or near net-shape bearing includes the step of placing an irradiated UHMWPE preform or puck of a volume sufficient to accommodate the bearing in a compression mold and compression molding the irradiated preform. The molding is accomplished by applying heat and pressure to form the preform into a desired shape. The compression molding induces biaxial orientation in the formed bearing.

62 Claims, 2 Drawing Sheets

U.S. PATENT DOCUMENTS

| | | | |
|---|---|---|---|
| 5,549,698 A | 8/1996 | Averill et al. | |
| 5,549,700 A | 8/1996 | Graham et al. | |
| 5,577,368 A | 11/1996 | Hamilton et al. | |
| 5,593,719 A | 1/1997 | Deamaley et al. | |
| 5,609,638 A | 3/1997 | Price et al. | |
| 5,645,882 A | 7/1997 | Llanos | |
| 5,650,485 A | 7/1997 | Sun et al. | |
| 5,674,293 A | 10/1997 | Armini et al. | |
| 5,702,448 A | 12/1997 | Buechel et al. | |
| 5,702,456 A | 12/1997 | Pienkowski | |
| 5,709,020 A | 1/1998 | Pienkowski et al. | |
| 5,728,748 A | 3/1998 | Sun et al. | |
| 5,753,182 A | 5/1998 | Higgins | |
| 5,876,453 A | 3/1999 | Beaty | |
| 5,879,388 A | 3/1999 | Pienkowski et al. | |
| 5,879,400 A | 3/1999 | Merrill et al. | |
| 5,879,407 A | 3/1999 | Waggener | |
| 6,017,975 A | 1/2000 | Saum et al. | |
| 6,143,232 A | 11/2000 | Rohr | |
| 6,168,626 B1 | 1/2001 | Hyon et al. | |
| 6,245,276 B1 * | 6/2001 | McNulty et al. | 264/322 |
| 6,432,349 B1 * | 8/2002 | Pletcher et al. | 264/479 |

OTHER PUBLICATIONS

Atkinson, J.R. et al., "Silane cross–linked polyethylene for prosthetic applications. Part I. Certain physical and mechanical properties related to the nature of the material", *Biomaterials*, 4:267 (1983).

Atkinson, J.R. et al., "Silane cross–linked polyethylene for prosthetic applications. Part II. Creep and wear behavior and a preliminary moulding test", *Biomaterials*, 5:326 (1984).

Bartel, D.L. et al., "The Effect of Conformity, Thickness, and Material on Stresses In Ultra–High Molecular Weight Components for Total Hip Replacement", *J. Bone & Joint Surgery*, 68–A(7):1041 (1986).

Bhateja, S.K., "Radiation–Induced Crystallinity Changes In Pressure–Crystallized Ultra–High Molecular Weight Polyethylene", *J. Macromol. Sci. Phys.*, B22(1): 159 (1983).

Bhateja, S.K. et al., "Radiation–Induced Crystallinity Changes in Linear Polyethylene", *J. Polym. Sci. Polym. Phys. Ed.*, 21: 523 (1983).

Bhateja, S.K. et al., "Radiation–Induced Crystallinity Changes in Polyethylene Blends", *J. Mater. Sci.*, 20:2389 (1985).

Birkinshaw, C. et al., "The Melting Behavior of Irradiated Polymers", *Thermochimica Acta*, 117: 365 (1987).

Bloebaum, R.D. et al., "Investigation of Early Surface Delamination Observed in Retrieved Heat–Pressed Tibial Inserts", *Clin. Orthop.*, 269: 120 (1991).

Bremmer, T. et al., "Peroxide Modification of Linear Low–Density Polyethylene: A Comparison of Dialkyl Peroxides", *J. Appl. Polym. Sci.*, 49: 785 (1993).

Brown, K.J. et al., "The Wear of Ultra–High Molecular Weight Polyethylene with Reference to Its Use in Prostheses", *Plastics in Medicine & Surgery Plastics & Rubber Institute*, London, 2.1 (1975).

Chen, C.J. et al., "Radiation–Induced crosslinking: II. Effect on the crystalline and amorphous densities polyethylene", *Coll. & Polym. Sci.*,269: 469 (1991).

Chen, Y.L. et al., "Photocrosslinking of Polyethylene I. Photoinitiators, Crosslinking Agent, and Reaction Kinetics", *J. Polym. Sci., Part A: Polym. Chem.* 27: 4051 (1989).

Chen, Y.L. et al., "Photocrosslinking of Polyethylene. II. Properties of Photocrosslinked Polyethylene", *J. Polym. Sci., Part A; Polym. Chem.*, 27: 4077 (1989).

Connelly, G.M. et al., "Fatigue Crack Propagation Behavior of Ultrahigh Molecular Weight Polyethylene", *J. Orthop. Res.*, 2: 119 (1984).

deBoer, A.P. et al., "Polyethylene Networks Crosslinked in Solution: Elastic Behavior and Oriented Crystallization. I. Crosslinking In Solution",*J. Polym. Sci., Polym. Phys. Ed.*, 14: 187 (1976).

deBoer, J. et al., "Crosslinking of Ultra–High Molecular Weight Polyethylene in the Melt by Means of 2,5–dimethyl–2,5–bis (tert–butyldioxy)–3–hexyne", *Makromol. Chem. Rapid Commun.*, 2: 749 (1981).

deBoer, J. et al., "Crosslinking of Ultra–High Molecular Weight Polyethylene in the Melt by Means of 2,5–dimethyl–2,5–bis (tert–butyldioxy)–3–hexyne: 2. Crystallization Behavior and Mechanical Properties", *Polymer*, 23: 1944 (1982).

deBoer, J. et al., "Crosslinking of Ultra–High Molecular Weight Polyethylene in the Oriented State with Dicumylperoxide", *Polymer*, 25: 513 (1984).

Dijkstra, D.J. et al., "Cross–linking of the ultra–high molecular weight polyethylene in the melt by means of electron bean irradiation", *Polymer*, 30: 866 (1989).

Ding Z.Y. et al., "Model Filled Polymers. VI. Determination of the Crosslink Density of Polymeric Beads by Swelling," *J. Polym. Sci., Part B: Poly. Phys.*, 29: 1035 (1991).

Eyerer, P. et al., "Property changes of UHMW polyethylene hip cup endoprostheses during implantation", *J. Biomed. Materials Res.*, 18: 1137 (1984).

Eyerer, P., "Polyethylene", *Concise Encyclopedia of Medical and Dental Implant Materials*, Pergamon Press, Oxford, 271 (1990).

Ferris, B.D., "A quantitative study of the tissue reaction and its relationship to debris production from joint implant", *J. Exp. Path.*, 71: 367 (1990).

Gielenz G. et al., "Crystalline and supermolecular structures in linear polyethylene irradiated with fast electrons", *Colloid & Polymer Sci.*, 260: 742 (1982).

Grobbelaar, C.J. et al., "The Radiation improvement of Polyethylene Prosthesis",*J. Bone & Joint Surgery*, 60–B(3): 370–374 (1978).

Grood, E.S. et al., "Analysis of retrieved implants: Crystallinity changes in ultrahigh molecular weight polyethylene", *J. Biomedical Materials Res.*, 16: 399 (1982).

Huang, D.D. et al., "Cyclic Fatigue Behaviors of UHMWPE and Enhanced UHMWPE", *Trans. 38$^{th}$ Ann. Mtg., Orthop. Res. Soc.*, 403 (1992).

Kamel, I. et al., "A Model for Radiation–Induced Changes in Ultrahigh–Molecular–Weight–Polyethylene", *J. Poly. Sci., Polym. Phys. Ed.*, 23:2407 (1985).

Kampouris, E.M. et al., "Benzyl Peroxide as a Crosslinking Agent for Polyethylene", *J. Appl. Polym. Sci.*, 34: 1209 (1987).

Kao, Y.H., "Crystallinity in chemically crosslinking low density polyethylenes: 1 Structural and fusion studies", *Polymer*, 27: 1669 (1986).

Katq, K. et al., "Structural Changes and Melting Behavior of γ–Irradiated Polyethylene",*Japanese J. Appl. Phys.*, 20: 691 (1981).

Kunert, K.A. et al., "Structural investigation of chemically crosslinked low density polyethylene", *Polymer*, 22: 1355 (1981).

Kurth, M. et al., "Effects of Radiation Sterilization on UHMW–Polyethylene", *Trans. Third World Biomaterials Congress*, 589 (1988).

Landy, M.M. et al., "Wear of Ultra–high–molecular–weight Polyethylene Components of 90 Retrieved Knee Prostheses", *J. Arthroplasty,* Supplement, 3: S73 (1988).

Lem, K. et al., "Rheological Properties of Polyethylenes Modified with Dicumyl Peroxide", *J. Appl. Polym. Sci.,* 27: 1367 (1982).

Li, S. et al., "Characterization and Description of an Enhanced High Molecular Weight Polyethylene for Orthopaedic Bearing Surfaces", *Trans. 16th Ann. Soc. Biomaterials Meeting,* Charleston, SC, 190 (1990).

Manley, T.R. et al., "The effects of varying peroxide concentration in crosslinked linear polyethylene", *Polymer,* 12:176 (1971).

McKellop, H. et al., "Friction, Lubrication and Wear of Polyethylene Metal and Polyethylene/Ceramic Hip Prostheses on a Joint Simulator", *Fourth World Biomaterials Congress,* Berlin, Apr., 118 (1992).

Minkova, L., "DSC of γ–irradiated ultra–high molecular weight polyethylene and high density polyethylene of normal molecular weight", *Colloid & Polymer Sci.,* 266: 6 (1988).

Minkova, L. et al., "Blends of normal high density and ultra–high molecular weight polyethylene, γ–irradiated at a low dose", *Colloid & Polymer Sci.,* 268: 1018 (1990).

Nagy, E.V. et al., "A Fourier transform infrared technique for the evaluation of polyethylene orthopaedic bearing materials", *Trans. 16th Ann. Soc. For Biomaterials Meeting,* Charleston, SC 109 (1990).

Narkis, M. et al., "Structure and Tensile Behavior of Irradiation–and Peroxide–Crosslinked Polyethylene", *J. Macromol. Sci.–Phys.,* B26(1): 37 (1987).

Nusbaum, H.J. et al., "The Effects of Radiation Sterilization on the Properties of Ultrahigh Molecular Weight Polyethylene", *J. Biomed. Materials Res.,* 13: 557 (1979).

Oonishi, H. et al., "Improvement of Polyethylene by Irradiation in Artificial Joints", *Radiat, Phys. Chem.,* 39: 495 (1992).

Oonishi, H. et al., "In Vivo and In Vitro Wear Behavior on Weightbearing Surfaces of Polyethylene Sockets Improved by Irradiation in Total Hip Prostheses", *Surface Modification Technologies V,* 101–115 (1992).

Painter, P.C., et al., "The Theory of Vibrational Spectroscopy and its Application to Polymeric Materials", Ed. John Wiley & Sons, New York, U.S.A., (1982).

Paul, J. P., "Forces Transmitted by Joints in the Human Body", *Proc. Instn. Mech. Engrs.* 181, Part 3J, Paper 8 (1966).

Qu, B.J. et al., "Photocross–linking of Low Density Polyethylene. I. Kinetics and Reaction Parameters", *J. Appl. Polym. Sci.,* 48: 701 (1993).

Qu, B.J. et al., "Photocross–linking of Low Density Polyethylene. II. Structure and Morphology", *J. Appl. Polym. Sci.,* 48: 711 (1993).

Rimnac, C.M. et al.,"Chemical and Mechanical Degradation of UHMWPE: Report of the Development of an In vitro Test", *J. Appl. Biomaterials,* 5:17 (1994).

Rimnac, C.M. et al., "Observations of Surface Damage and Degradation on Retrieved PCA Knee Implants", *Trans. 38th Ann. Orthopaedic Res. Society,* Washington, D.C., 330 (1992).

Rimnac, C.M. et al., "Post–Irradiation Aging of Ultra–High Molecular Weight Polyethylene", *J. Bone & Joint Surgery,* 76–A(7): 1052 (1994).

Roe, R. et al., "Effect of radiation sterilization and aging on ultrahigh molecular weight polyethylene", *J. Biomed. Mat. Res.,* 15: 209 (1981).

Rose, R.M. et al., "On the True Wear Rate of Ultra–High Molecular Weight Polyethylene in the Total Hip Prosthesis", *J. Bone & Joint Surgery,* 62A(4): 537(1980).

Rose, R.M. et al., "Exploratory Investigations in the Structure Dependence of the Wear Resistance of Polyethylene", *Wear,* 77:89 (1982).

Rostoker, W. et al., "The Appearances of Wear on Polyethylene—A Comparison of in vivo and in vitro Wear Surfaces", *J. Biomed. Materials Res.,* 12:317 (1978).

Seedhom, B.B. et al., "Wear of Solid Phase Formed High Density Polyethylene in Relation to the Life of Artificial Hips and Knees", *Wear,* 24: 35 (1973).

Shen, C. et al., "The Friction and Wear Behavior of Irradiated Very High Molecular Weight Polyethylene", *Wear,* 30:349 (1974).

Shinde, A. et al., "Irradiation of Ultrahigh–MolecularWeight Polyethylene", *J. Polym. Sci. Polym. Phys. Ed.,* 23: 1681 (1985).

Spruiell, J.E. et al., "Methods of Experimental Physics", L. Marton & C. Marton Eds., vol. 16, Part B Academic Press, New York (1980).

Streicher, R.M., "Ionizing irradiation for sterilization and modification of high molecular weight polyethylenes", *Plastics & Rubber Processing & Applications,* 10: 221 (1988).

Streicher, R.M., "Investigation on Sterilization and Modification of High Molecular Weight Polyethylenes by Ionizing Irradiation", *Beta–gamma,* 1/89:34–43 (1989).

Swanson, S.A.V. et al., "Chapter 3, Friction, Lubrication and Wear", *The Scientific Basis of Joint Replacement,* Pittman Medical Publishing Co., Ltd. (1977).

Wang, X. et al., "Melting of Ultrahigh Molecular Weight Polyethylene", *J. App. Polymer Sci.,* 34:593 (1987).

Wright, T.M. et al., "The effect of carbon fiber reinforcement on contact area, contact pressure, and time–dependent deformation in polyethylene tibial components", *J. Biomed. Materials Res.,* 15:719 (1981).

Zachariades, A.E., "A New Class of UHMWPE Orthopaedic Prosthetic Devices with Enhanced Mechanical Properties", *Trans. Fourth World Biomaterials Congress,* Berlin 623 (1992).

Zhao, Y. et al., "Effect of Irradiation on Crystallinity and Mechanical Properties of Ultrahigh Molecular Weight Polyethylene", *J. Appl. Polym. Sci.,* 50:1797 (1993).

"News You Can Use", vol. II, No. 2 (May 1996).

"For the Tough Jobs: 1990 UHMW Polymer", Himont, Inc. (1988).

"Abrasion–Resistant 1900 UHMW Polymer", Hercules, Inc. (1979).

"Technical Information: 1900 Ultrahigh Molecular Weight Polymer, General Information and Applications", *Bulletin JPE–101A,* Hercules, U.S.A., Inc., (1989).

"Technical Information: 1900 Ultrahigh Molecular Weight Polymer, Nuclear Radiation Effects", *Bulletin HPE–111,* Himont U.S.A., Inc. (1985).

"Technical Information: 1900 Ultrahigh Molecular Weight Polymer, Effect of Polymer Modification", *Bulletin HPE–116,* Himont U.S.A., Inc. (1987).

"Ultra–High Molecular Weight Polyethylene as Biomaterial In Orthopaedic Surgery", Hogrefe & Huber Publishers (1991).

Appleby, R.W. et al., "Post–gamma irradiation cross–linking polyethylene tape by acetylene treatment", *J. Material Sci.,* 29:227–231 (1994).

Higgins, J.C. et al.,"Evaluation of Free Radical Reduction Treatments for UHMWPE", *Proceedings of the 42th Annual Mtg., Orthopaedic Res. Soc.,* Feb. 19–22:485 (1996).

Jasty, M. et al., "Marked Improvement in the Wear Resistance of a New Form of UHMPWE in a Physiologic Hip Simulator", *Trans. 43th Ann. Mtg., Orthopaedic Research Soc.,* San Francisco, CA, Feb. 9–13;785 (1997).

Jasty, M. et al, "Marked Improvement in the Wear Resistance of a New Form of UHMPWE in a Physiologic Hip Simulator",*Trans. Soc. Biomaterials,* vol. XX, p 71, 23$^{nd}$ *Ann. Mtg. Soc. for Biomaterials,* New Orleans, Louisiana, U.S.A., Apr. 30–May 4:157 (1997).

Streicher, Influence of Ionizing Irradiation in Air and Nitrogen for Sterilization of Surgical Grade Polyethylene for Implants, *Radiat. Phys. Chem.,* vol. 31, Nos. 4–6; 693–698 (1988).

Pleiss et al., "The Improvement of Polyethylene Prosthesis Through Radiation Crosslinking", *Radiat. Phys. Chem.,* 9: 647–652 (1977).

Streicher, "The Behavior of UHMW–PE when Subjected to Sterilization by Ionizing Radiation", Ultra–High Molecular Weight Polyethylene as Biomaterial in Orthopedic Surgery, 66–73 (1990).

Saunders, C. et al., "Radiation Effects on Microorganisms and Polymers for Medical Products", *Medical Device & Diagnostic Industry,* 222:89–22 (1993).

Kang et al., "The Radiation Chemistry of Polyethylene IX. Temperature Coefficient of Cross–linking and Other Effects", *J. Amer. Chem. Society,* 89(9): 1980–1986 (1967).

Rose et al., "Radiation Sterilization and the Wear Rate of Polyethylene", *J. Orthopaedic Res. Society,* 2(4): 393–499 (1984).

Oonishi, H. et al., "Super Low Wear Cross–Linked UHM-WPE by Heavy High–Dose Gamma Radiation", *WPOS 2$^{nd}$ Congress of Hip Section,* 61 (1996).

Jahan et al., "Combined chemical and mechanical effects on the free radicals in UHMWPE joints during implantation", *J. Biomed. Materials Res.,* 25: 1005–1016 (1991).

"Standard Practice for Dosimetry in an Electron Bean Facility for Radiation Processing at Energies Between 300 keV and 25 keV",*Am. Soc. for Testing & Materials,* Designation: E1649–94, 870–88 (1995).

Oonishi, H. et al., "The Low Wear of Cross–Linked Polyethylene Socket in Total Hip Prostheses", Encyclopedic Handbook of Biomaterials & Bioengineering, vol. 2, Marcel Dekker, Inc., 1853–1868 (1995).

Atkinson, J. et al., "The nature of silane cross–linked HDPE is discussed. Creep and wear tests indicate its potential as a possible replacement for high molecular weight polyethylene in prostheses", *Polymers in Medicine and Surgery, Conf. Held by Plastics and Rubber Institute and Biological Engineering Soc.,* UK. Sep., P4/1–P4/9 (1986).

Jones, W. et al., Effect of γ Irradiation on the Friction and Wear of Ultrahigh Molecular Weight Polyethylene, *Wear* 70: 77–92 (1981).

Gent, A. et al., "Elastic Behavior, Birefringence, and Swelling of Amorphous Polyethylene Networks", *J. Polymer Sci.* 5: 47–60 (1967).

Zoepfl, F. et al., "Differential Scanning Calorimetry Studies of Irradiated Polyethylene: I. Melting Temperatures and Fusion Endotherms", *J. Polymer Sci. Polym. Chem. Ed.,* 22: 2017–2032 (1984).

Zoepfl, F. et al., "Differential Scanning Calorimetry Studies of Irradiated Polyethylene: II. The Effect of Oxygen", *J. Polymer Sci. Polym. Chem. Ed.,* 22: 2032–2045 (1984).

Mandelkern, L. et al., "Fusion of Polymer Networks Formed from Linear Polyethylene: Effect of Intermolecular Order", contribution from the General Electric Research Laboratory and from the Polymer Structure Section, National Bureau of Standards 82: 46–53 (1960).

Muratoglu, O.K. et al., "A Comparison of 5 Different Types of Highly Crosslinked UHMWPES: Physical Properties and Wear Behavior", *45$^{th}$ Annual Meeting, Orthopaedic Research Society,* Anaheim, CA, Feb. 1–4, 77 (1999).

Muratoglu, O.K. et al., "A Novel Method of Crosslinking UHMWPE to Improve Wear With Little or No Sacrifice on Mechanical Properties", *45$^{th}$ Annual Meeting, Orthopaedic Research Society,* Anaheim, CA, Feb. 1–4, 829 (1999).

Muratoglu, O.K. et al., "Electron Beam Cross Linking of UHMWPE At Room Remperature, A Candidate Bearing Material for Total Joint Anthroplasty", *23rd Annual Meeting of the Society for Biomaterials,* New Orleans, Louisiana, Apr. 30–May 4, 74 (1997).

Matsubara K. et al., "The Wear Properties of High–Density Polyethylene Irradiated by Gamma Rays", *Wear* 10: 214 (1967).

McKellop, H. et al., "Increased Wear of UHMW Polyethylene After Gamma Radiation Sterilization", *Trans. 26$^{th}$ Ann. ORS,* Atlanta, Georgia, Feb. 5–7 (1980).

McKellop, H., "The Effect of Radiation and Ethylene Oxide Sterilization on the Wear of UHMW Polyethylene", *7$^{th}$ European Conference on Biomaterials,* Sep. 8–11, (1987).

Shen, F.S. et al., "Irradiation of Chemically Crosslinked Ultrahigh Molecular Weight Polyethylene",*J. Polymer Sci.: Part B: Polymer Phys.* 34: 1063–1077 (1996).

Oka, M. et al., "Wear–Resistant Properties of Newly Improved UHMWPE", *Trans. Fifth World Biomaterials Congress,* Toronto, Canada 520, (May 2–Jun. 2, 1996).

Bellare, A. et al., "Definition, Morphology and Wear Behavior of Polyethylene", *Trans. 23$^{rd}$ Ann. Mtg., Soc. Biomaterials,* New Orleans, Louisiana, 75 (Apr. 30–May 4, 1997).

Clarke, I.C. et al., "Simulator Wear Study of High–Dose Gamma–Irradiated UHMWPE Cups", *Trans. 23$^{rd}$, Ann. Mtg. Soc. Biomaterials,* New Orleans, LA, 71, (Apr. 30–May 4, 1997).

Taylor, G. et al., "Stability of $N_2$ Packaged Gamma Irradiated UHMWPE", *Trans. 23$^{rd}$ Ann. Mtg. Soc. Biomaterials,* New Orleans, LA, 421, (Apr. 30–May 4, 1997).

Taylor, G. et al., "Stability of $N_2$ Packaged Gamma Irradiated UHMWPE", *Trans. 43$^{rd}$ Ann. Mtg. Orthopaedic Res. Soc.,* San Francisco, California, 776b (Feb. 9–13, 1997).

McKellop, H. et al., "The Effect of Sterilization Method, Calcium Stearate and Molecular Weight on Wear of UHM-WPE Acetabular Cups", *Trans. 23$^{th}$ Ann. Mtg., Soc. Biomaterials,* New Orleans, LA, 43 (Apr. 30–May 4, 1997).

McKellop, H. et al., "Effect of Sterilization Method on the Wear Rate of UHMW Polyethylene Acetabular Cups in a Hip Simulator", *Trans. Ann. Mtg. Orthopaedic Res. Soc.* San Francisco, CA, 7, 94–16 Feb. 9–13 (1997).

McKellop, H. et al., "Wear of UHMWPE Acetabular Cups After Gamma Sterilization in Nitrogen, Thermal Stabilization and Artificial Aging", *Trans. 23rd Mtg., Soc. Biomaterials,* New Orleans, LA, Apr. 30–May 4, 45 (1997).

Wang, A. et al., "Effect of Radiation Dosage on the Wear of Stabilized UHMWPE Evaluated by Hip and Knee Joint Simulators", *Trans. 23rd , Mtg. Soc. Biomaterials,* New Orleans, LA, 394 (Apr. 30–May 4, 1997).

Wang, A. et al., "Wear Mechanisms and Wear Testing of Ultra–High Molecular Weight Polyethylene in Total Joint Replacements", Hand–Out for Polyethylene Wear in Orthopaedic Implants Workshop, *Trans. 23th Ann. Mtg., Soc. Biomaterials,* New Orleans, LA (Apr. 30–May 4, 1997).

Yu, Y.J. et al., "Oxidation of UHMWPE Acetabular Cups After Sterilization and Wear Testing in a Hip Joint Simulator", *Trans. 43rd Ann. Mtg. Orthopaedic Res. Soc.* San Francisco, CA, 778 (Feb. 9–13, 1997).

Roe, R. et al., "Effect of Radiation Sterilization and Aging on Ultrahigh Molecular Weight Polyethylene", *Journal of Biomedical Materials Research,* 15:209–230 (1981).

Li, S. et al., "Chemical Degradation of Polyethylene in Hip and Knee Replacements", *38th Ann. Mtg., Orthopaedic Research Society,* Washington, D.C., 41, (Feb. 7–20, 1992).

Kurtz, S.M. et al., "Post–Irradiation Aging and The Stresses in UHMWPE Components for Total Joint Replacement", *40th Ann. Mtg. Orthopaedic Research Society,* New Orleans, LA, 584, (Feb. 21–24, 1994).

Lancaster et al., "Friction and Wear", in Jenkins (ed): Polymer Science, 959, 1045, North Holland Publishing Company (1972).

McKellop, H. et al., "Accelerated Aging of Irradiated UHMW Polyethylene for Wear Evaluations", *42nd Annual Meeting, Orthopaedic Research Society,* Atlanta, Georgia, 483, (Feb. 19–22, 1996).

Blunn, G.W. et al., "The Effect of Oxidation on the Wear of Untreated and Stabilized UHMWPE", *42nd Annual Meeting, Orthopaedic Research Society,* Atlanta, Georgia, 482 (Feb. 19–22, 1996).

"Duration™ Stabilized UHMWPE: an UHMWPE with Superior Wear and Oxidation Resistance; Technical Development and Scientific Evaluation", (Cover sheet and reference page) (Undated).

Sun, D.C. et al., "The Origin of the White Band Observed in Direct Compression Molded UHMWPE Inserts", *20th Annual Meeting Society for Biomaterials,* 121 (Apr. 5–9, 1994).

Sun, D.C. et al.,"On the Origin of a Subsurface Oxidation Maximum and its Relationship to the Performance of UHMWPE Implants", *21st Annual Meeting, Society for Biochemicals,* San Francisco, CA, 362: (Mar. 18–22, 1995).

Premnath, V. et al., "Melt Irradiated UHMWPE for Total Hip Replacement: Synthesis & Properties", *43rd Annual Meeting, Orthopedic Res. Soc.,* San Francisco, CA, 91–16, (Feb. 9–13, 1997).

Muratoglu, O.K. et al., "The Effect of Temperature on Radiation Crosslinking of UHMWPE for Use in Total Hip Arthroplasty", *46th Annual Meeting, Orthopaedic Res. Soc.,* Orlando, FL, 0574 (Mar. 12–15, 2000).

D.C. Sun, C. Stark., J. H. Dumbleton, "Development of an Accelerated Aging Method For Evaluation of Long–term Irradiation Effects on UHMWPE Implants", *Polymer Preprints,* vol. 35, No. 2, pp. 969–970, (1994).

A.F. Booth, "Industrial Sterilization Technologies: New and Old Trends Shape Manufacturer Choices", *Medical Device & Diagnostic Industry,* pp. 64–72, Feb. (1995).

B. Hinsch, "Sterilization Methods for Implants Made of UHMWPE", in *Ultra–High Molecular Weight Polyethylene as Biomaterials in Orthopedic Surgery,* Toronto: Hogrefe & Huber Publishers, pp. 63–65, (1991).

"Irradiation Effects on Polymers", edited by D.W. Clegg and A.A. Collyer, *Elsevier Applied Science,* London, (1991).

"Radiation Effects on Polymers", edited by R. L. Clough and S. W. Shalaby, *ACS Symposium Series 475,* (1991).

P. Eyerer, M. Kurth, H.A. McKellop and T. Mittimeier, "Characterization of UHMWPE hip cups run on joint stimulators", *J. Biomedical Materials Research,* vol. 21, pp. 275–291, (1987).

A. Wang, D.C. Sun, C.Stark, J.H. Dumbleton, *Wear,* pp. 181–183:241–249 (1995).

A. Wang, C. Stark, J.H. Dumbleton, "Tole of cyclic plastic deformation in the wear of UHMWPE acetabular cups", *Journal of Biomedical Materials Research,* vol. 29, pp. 619–626, (1995).

A. Edidin et al., "Enhancement of multitaxial mechanical behavior by slot drawing of UHMWPE: a candidate biomaterial for total knee anthroplasty," *46th Annual Mtg. Orthopaedic. Res. Soc.,* Mar. 12–15, Orlando, FL (2000).

* cited by examiner

ORIENTED, CROSS-LINKED UHMWPE MOLDING FOR ORTHOPAEDIC APPLICATIONS

This patent application claims priority to a U.S. provisional patent application, Ser. No. 60/236,958, filed Sep. 29, 2000, the disclosure of which is hereby incorporated by reference.

FIELD OF THE INVENTION

The present invention relates to a compression molding process for forming orthopaedic implant prosthesis bearings having increased wear resistance and improved mechanical properties. The present invention particularly relates to improved bearings for use in orthopaedic implant prosthesis and to methods for making polyethylene bearings by molding a cross-linked preform via the application of sufficient heat and pressure in such a way as to induce orientation in molded bearings.

BACKGROUND OF THE INVENTION

Ultrahigh molecular weight polyethylene (UHMWPE) has been the material of choice for articulating surface applications for three decades. Such UHMWPE resin is commonly used for implantable prosthesis bearings, such as acetabular bearings, glenoid bearings, tibial bearings, and the like, for use in hip, knee, shoulder and elbow prostheses. In that time many improvements have been introduced, most notably irradiation of the polyethylene to induce crosslinking. In fact, the improved wear characteristics of the polyethylene have been largely attributed to such cross-linking procedures. Typically, a bar stock or preform, or a molded or machined bearing is irradiated and subsequently heat treated or heat annealed. The irradiation generates molecular cross-links and free radicals. Such cross-linking creates a 3-dimensional network in the polymer which renders it more resistant to abrasive wear in multiple directions. In addition, the free radicals formed upon irradiation of UHMWPE can also participate in oxidation reactions, which reduce the molecular weight of the polymer via chain scission, leading to degradation of physical properties, embrittlement, and an increase in wear rate. The free radicals may be very long-lived, often several years, so that oxidation can continue over an extended period of time. Processes that tend to substantially eliminate residual free radicals induced by such irradiation tend to provide polyethylene with improved oxidation resistance. Typical processes for quenching free radicals in UHMWPE induced by irradiation involve elimination of the free radicals with heat treatments.

The bearings may be formed from polyethylene by direct compression molding processes or by machining the required bearing shapes from mill shapes, such as sheet or bar stock. Molding processes may be performed on unirradiated or irradiated polyethylene.

Processes to improve the material properties of the polyethylene, such as toughness, and the like, are yet sought. It is appreciated that such processes desirably do not compromise the advances in wear properties that have been made. Wear-resistant materials reduce wear debris-associated maladies, such as bone and soft tissue deterioration, wear debris-induced osteolysis, and the like. Such maladies may lead to implant loosening and possibly necessitate revision surgery.

Reference is made to a number of prior art references as follows:

1. U.S. Pat. No. 5,728,748, and its counterparts all relating to the same application, "Non-Oxidizing Polymeric Medical Implant," to Sun, et al.
2. U.S. Pat. No. 5,879,400, "Melt-Irradiated Ultra High Molecular Weight Polyethylene Prosthetic Devices," to Merrill et al.
3. U.S. Pat. No. 6,017,975, "Process for Medical Implant of Cross-Linked Ultrahigh Molecular Weight Polyethylene Having Improved Balance of Wear Properties and Oxidation Resistance," to Saum, et al.
4. U.S. Pat. No. 6,228,900, "Crosslinking of Polyethylene for Low Wear Using Radiation and Thermal Treatments," to Shen et al.
5. U.S. Pat. No. 6,168,626, "Ultra High Molecular Weight Polyethylene Molded Article for Artificial Joints and Method of Preparing the Same," to Hyon et al.
6. U.S. Pat. No. 6,245,276, "Method for Molding a Cross-Linked Preform," to McNulty et al.
7. U.S. Pat. No. 6,281,264, "Chemically Crosslinked Ultrahigh Molecular Weight Polyethylene for Artificial Human Joints," to Salovey et al.

The above references teach the general concepts involved in forming or consolidating polyethylene resin directly into a component or a stock form from which the component is made, gamma or other irradiation of the component or the stock form, and subsequent heat treating (including annealing or remelting) of the component or stock form. The above references also teach the general concepts of compression molding and the appropriate apparatuses used therein. The disclosures of these above-listed references are incorporated herein for purposes of establishing the nature of polyethylene resin, the irradiation steps and options, and the heat treating steps and options.

SUMMARY OF THE INVENTION

The present invention provides UHMWPE bearings with improved mechanical properties, improved oxidation resistance and increased wear resistance. The polyethylenes prepared by the processes of the present invention also reduces the amount of wear debris generated from UHMWPE bearings. Typically, the polyethylene may be ultrahigh molecular weight polyethylene (UHMWPE), although it will be appreciated that the processes of the present invention may be used with various types of polyethylene.

The present invention is directed to a process for molding a bearing, near net-shape bearing, or net-shape bearing from a preform, which has been previously cross-linked, by obtaining such a preform and placing it in a press mold defining the desired bearing shape, or near net-shape, and applying heat and pressure in the mold to form the bearing in such a way as to orient the polyethylene. What is meant herein by the term "net-shape bearing" is a bearing that is in a shape or condition that is satisfactory for use in a prosthetic implant upon removal of the bearing from a compression molding die without requiring any additional machining. The term "near net-shape", on the other hand, is meant herein to define a bearing which requires a small degree of further manipulation, such as machining, to produce the final bearing with such further manipulation being performed on surfaces of the bearing other than the articulating (i.e., bearing) surface of the bearing. What is meant herein by the term "bearing" is an orthopaedic implant prosthetic bearing of any type, condition, shape, or configuration. As such, the term "bearing", amongst others, includes both net-shape bearings and near net-shape bearings.

The present invention is also directed to a compression molding process that induces biaxial orientation in the molded bearing to improve its wear characteristics and mechanical properties. In some embodiments, the preforms may be made from consolidated UHMWPE stock which has been irradiated. In other embodiments, the UHMWPE stock may be pre-annealed or pressure crystallized, or a combination thereof, to further enhance its mechanical properties. In an alternate embodiment, the irradiated UHMWPE preform may be heated or otherwise treated to substantially quench free radicals present in the irradiated preform.

Additional features of the present invention will become apparent to those skilled in the art upon consideration of the following detailed description of invention exemplifying the best mode of carrying out the invention as presently perceived.

DETAILED DESCRIPTION OF THE INVENTION

Figure 1:
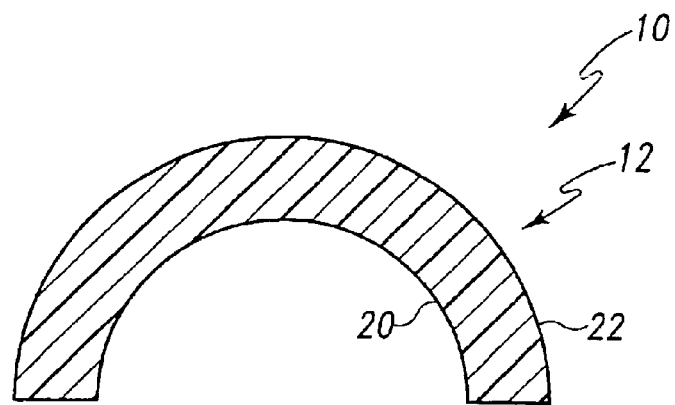
FIG. 1 is a schematic view of an implantable prosthetic bearing that may be produced by processes described herein.

While the invention is susceptible to various modifications and alternative forms, specific embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

A typical prosthetic bearing design includes an articulating or bearing surface on which either a natural bone structure or a prosthetic component articulates. In addition, a typical prosthetic bearing design also includes an engaging surface which may include locking features in the form of mechanisms such as pins, tabs, tapered posts, or the like for locking or otherwise securing the bearing to either another component associated with a prosthetic assembly (e.g., a metal shell or tray) or to the bone itself.

Figure 2:
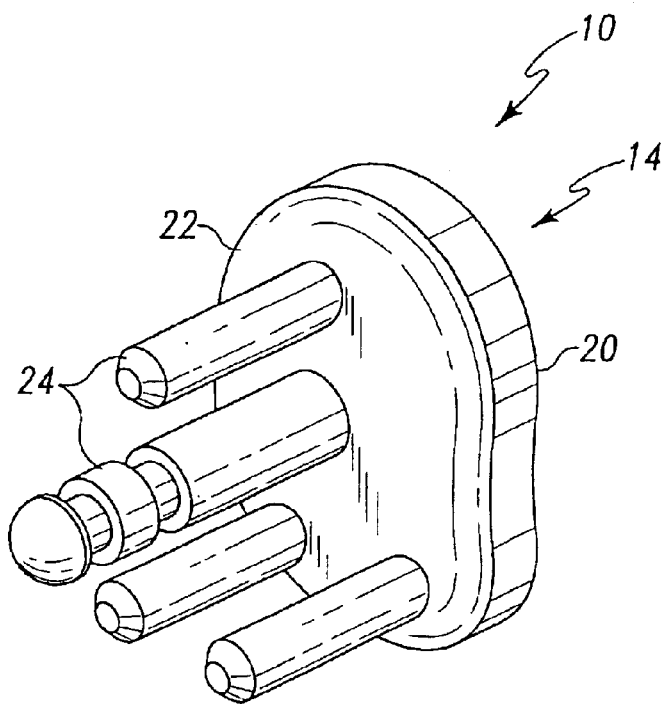
FIG. 2 is a perspective view of an implantable glenoid bearing prosthesis that may be produced by processes described herein.
Figure 3:
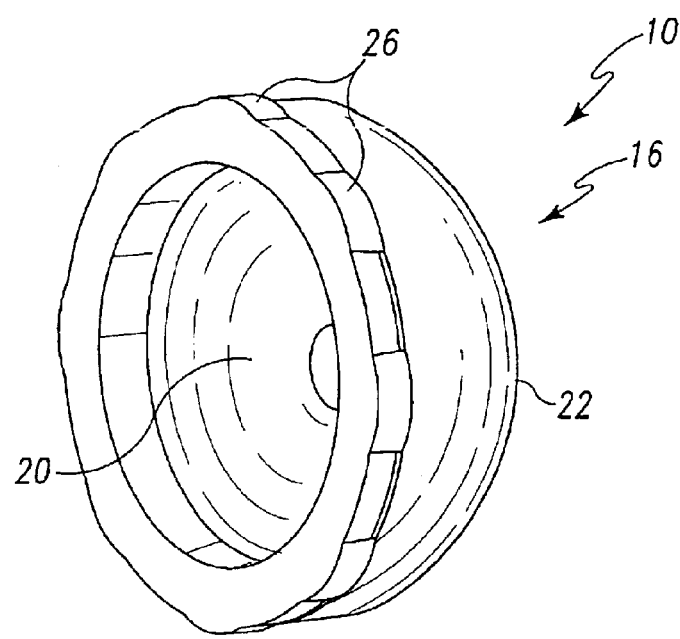
FIG. 3 is a perspective view of an implantable acetabular bearing prosthesis that may be produced by processes described herein.
Figure 4:
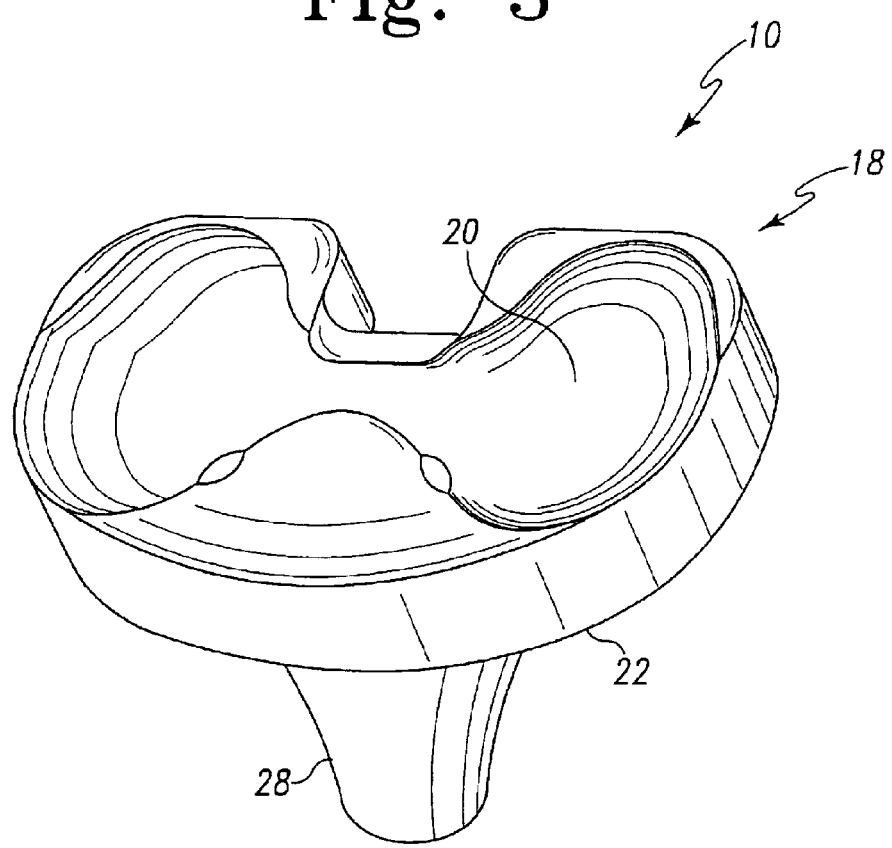
FIG. 4 is a perspective view of an implantable tibial bearing prosthesis that may be produced by processes described herein.

Referring now to FIGS. 1–4, there is shown an implantable prosthetic bearing 10. The bearing 10 is shown schematically as a bearing 12 in FIG. 1, whereas specific exemplary embodiments of the prosthetic bearing 10, such as a glenoid bearing 14 for implantation into a glenoid of a patient (not shown), an acetabular bearing 16 for implantation into an acetabulum of a patient (not shown), and a tibial bearing 18 for implantation into a tibia of a patient (not shown) are shown in FIGS. 2–4, respectively. Each of the embodiments of the prosthetic bearing 10 includes an articulating or bearing surface 20 on which a natural or prosthetic component bears. For example, in the case of the glenoid bearing 14, a natural or prosthetic humeral head (not shown) bears on the articulating surface 20. Similarly, in the case of a acetabular bearing 16, a natural or prosthetic femoral head (not shown) bears on the articulating surface 20. Moreover, in the case of the tibial bearing 18, a pair of natural or prosthetic femoral condyles (not shown) bear on the articulating surface 20.

Each of the prosthetic bearings 10 also includes an engaging surface 22 which may have a number of features defined therein for engaging either another prosthetic component or the bone into which the bearing 10 is to be implanted. For example, in the case of the glenoid bearing 14, a number of pins or pegs 24 may be defined in the engaging surface 22 thereof. The pegs 24 are received into a number of corresponding holes (not shown) formed in the glenoid surface of the patient. The pins 24 are typically held in place with the use of bone cement. Moreover, if the glenoid bearing 14 is utilized in conjunction with an implanted metal shell, the engaging surface 22 of the bearing 14 may be configured with a tapered post (not shown) or the like for securing the glenoid bearing 14 to the shell.

In the case of the acetabular bearing 16, a number of keying tabs 26 are defined in the engaging surface 22 along the outer annular surface thereof. The keying tabs 26 are received into a number of corresponding keying slots (not shown) defined in an implanted metal acetabular shell (not shown) in order to prevent rotation of the acetabular bearing 16 relative to the implanted shell. In the case of fixation of the acetabular bearing 16 directly to the acetabulum of the patient (i.e., without the use of a metal shell), the engaging surface 22 of the bearing 16 may alternatively be configured with a number of posts or pegs (not shown) which are received into a number of corresponding holes formed in the patient's acetabulum. In such a case, the posts or pegs are typically held in place with the use of bone cement. Moreover, it should be appreciated that the acetabular bearing 16 may be cemented to the patient's acetabulum without the use of posts or pegs on the engaging surface 22 thereof.

In the case of the tibial bearing 18, a tapered post 28 is defined in the engaging surface 22 thereof. The tapered post 28 is received into a corresponding tapered bore (not shown) defined in an implanted tibial tray (not shown) of a knee prosthesis (not shown). It should be appreciated that the engaging surface 22 of the tibial bearing 18 may also be configured with features to allow the tibial bearing 18 to be secured directly to the tibia without the use of an implanted tray (e.g., by use of bone cement).

The present invention pertains to fabrication of such an orthopaedic implant prosthetic bearing 10 by compression molding a preform, by the application of heat and pressure, in a mold defining the shape of the bearing 10. The process of the present invention may be used to mold net-shape bearings directly to provide a finish which is satisfactory for an articular (bearing) surface. It is appreciated that smoother bearing surfaces may be made by molding processes than by machining processes. However, the process of the present invention may also be used to mold near net-shape bearings that require a small degree of additional machining. In either case, the preform may be fabricated from an olefinic resin, typically a polyethylene resin, such as an ultrahigh molecular weight polyethylene (UHMWPE) resin. It is further appreciated that other polyethylenes such as high molecular weight polyethylene, high density polyethylene, high molecular weight high density polyethylene, and the like may be fabricated into bearings using the processes described herein. The term "preform" as used herein refers to an article that has been consolidated, such as by ram extrusion or compression molding of polyethylene resin particles into rods, sheets, blocks, slabs, or the like. The term "preform" also includes a preform "puck" which may be prepared by intermediate machining of a commercially available preform. Preform pucks are of a size and mass suitable to be placed into a bearing compression molding die. The shape of the preform or puck may or may not be similar to the final net shape component. In addition, the formed bearing following compression molding may be either the actual desired bearing configuration or a blank that can be machined subsequently to produce the desired bearing geometry. Such preforms may be obtained or machined from commercially available UHMWPE, for example GUR 4150 HP ram extruded UHMWPE rods from PolyHi Solidur (Fort Wayne, Ind.). The starting preform may be pressure recrystallized as described in U.S. Pat. No. 5,478,906 and in U.S. Pat. No. 6,017,975. The starting preform may be optionally annealed, as described in U.S. Pat. No. 6,017,975, prior to irradiation. This pre-annealing step may be conducted in a substantially oxygen-free atmosphere. It is appreciated that the preform of the present invention may be formed from a wide variety of crude or processed plastic resins suitable for use in orthopaedics, that can be converted by manufacture into a finished bearing. It is further appreciated that the current invention contemplates cross-linking of the polyethylene prior to intermediate machining of a commercial stock into a preform puck.

An exemplary embodiment of the current invention includes a process that includes the steps of irradiating a polyethylene preform to form free radicals and cross-link the polyethylene and compression molding the preform by the application of heat and pressure to form a bearing, net-shape bearing, or near net-shape bearing. The compression molding process is performed in a manner to provide an oriented bearing.

The preform is irradiated, preferably with gamma radiation; however, electron beam or X-ray radiation may also be used. The preform is irradiated with gamma radiation at a dose of about 0.5 Mrad to about 50 Mrad, preferably about 5.1 Mrad to about 15 Mrad, using methods known in the art. The irradiation process may be optionally performed under vacuum or in an inert or substantially oxygen-free atmosphere by placing the preform in a bag, which includes materials such as aluminum foil, polyethylene, and the like, suitable for such irradiation processes. The bag may be optionally evacuated and the atmosphere substantially replaced with an inert gas such as nitrogen, argon, and the like. It will be appreciated, however, that acceptable results may be achieved for certain bearing configurations when the irradiation process is carried out under atmospheric conditions, i.e., with some oxygen present.

The compression molding process is performed in such a manner as to induce two-dimensional flow of the polyethylene in a plane, referred to hereinafter as "planar flow." Such a plane is transverse to any axis which is parallel with the direction of compression. It should be appreciated that any such axis parallel to the direction of compression passes through, and as a result does not lie in, this transverse plane. The induction of planar flow in the preform creates molecular orientation, preferably biaxial molecular orientation, in the plane of the formed bearing that is transverse to the compression direction. However, depending upon the manner in which the preform is placed into the compression mold, and the dimensions of the preform relative to the mold cavity, varying levels of symmetry may be thus imparted to the resulting formed bearing. It is therefore appreciated that the resulting planar flow may also be asymmetric, and in certain cases, the planar flow will adopt a substantially uniaxial orientation transverse to the compression direction in certain bearing configurations prepared by processes described herein.

In the case of bearings possessing a substantially circular or elliptical cross-section, the biaxial orientation in the formed bearing is preferably radially-disposed biaxial molecular orientation. The term "radially-disposed" is defined herein to mean an orientation in which a structure such as a molecular chain or a crystal structure extends radially outward from the center, or a point near the center, of the compression force, within a plane transverse to the compression force. The biaxial orientation present in the formed bearing may also be present as biaxial crystal orientation.

The degree of biaxial orientation present in the formed bearing may be assessed by methods known in the art such as thermal mechanical analysis (TMA), thermal shrinkage, X-ray diffraction (XRD), Crossed Polarizer Microscopy, and others. Thermal mechanical analysis includes the measurement of thermal relaxation properties. Thermal expansion and contraction of oriented polyethylenes can be determined using instruments such as the 2940 Thermal Mechanical Tester, commercially available from TA Instruments, New Castle, Del.

Materials that are biaxially oriented tend to undergo significant contraction in the two directions (i.e. dimensions) transverse to the compression direction, namely in the transverse plane, when heated to a temperature at or near the melting point of the material. This thermally-induced contraction is typically irreversible, such that the material does not return to the original volume upon subsequent cooling. In contrast, isotropic materials, those materials that do not exhibit significant orientation in any direction, may be characterized by their exhibiting of thermal expansion in all directions when heated near the melting point of the material. Furthermore, such thermal expansion is often reversible; the material returns to a volume approximating the original volume when it is cooled. Polyethylenes prepared according to the processes of the current invention are expected to have increased wear resistance and improved mechanical properties.

Under certain variations of the process, the compression molding step has the additional benefit of substantially eliminating residual free radicals in the UHMWPE. Such an elimination of free radicals may eliminate the need for, and thus make optional, a discrete quenching step following the irradiation step, such as a quenching step involving heat treatment. Compression molding induces elongational shear flow, or melt flow, which may account for this advantage, by promoting effective recombination of free radicals present in the polymer. However, it should be appreciated that, if desired, a discrete quenching step (e.g., heat treatment) may be utilized prior to compression molding of the preform.

Free radical populations present in the formed bearing may be measured by such techniques as electron paramagnetic resonance (EPR), and the like. Populations of free radicals following the compression molding step are preferably at levels comparable to the preform prior to irradiation. The compression molding step may reduce free radical populations by as much as about 90% or greater, preferably by as much as about 95% or greater, more preferably by as much as about 99% or greater, from those levels measured soon after irradiation, as determined by measurement methods like those mentioned above. It is appreciated that the occurrence of further cross-linking of the polyethylene and accompanying improvements in both the mechanical properties and wear characteristics benefitting the UHMWPE bearings may thus be achieved.

The preform may be heated within the molding equipment to a temperature high enough to allow deformation under compression, usually to a temperature above the melting temperature of the polyethylene, illustratively at temperatures from about 110° C. to about 250° C., preferably at temperatures from about 130° C. to about 240° C., and more preferably at temperatures from about 138° C. to about 216° C. It is appreciated that in some embodiments, the preform is heated to a temperature below the melting temperature of the polyethylene, but still high enough to allow deformation of the preform in the compression molding process.

In an alternative embodiment, the preform may be heated to a temperature above ambient temperature prior to placement in the molding equipment. After placement in the molding equipment the temperature may be adjusted if necessary to a temperature suitable for compression molding, such as the temperature within the ranges described above. It is appreciated that certain equipment configurations or fabrication processes may require either one or a combination of both of these heating steps as the process demands.

Prior to the application of pressure sufficient to effect compression molding, it may be desirable to allow the puck or preform to reach a degree of thermal equilibrium during a "melt-soak stage." The term "melt-soak stage" as used herein refers to a period of time during which the preform is held at a temperature suitable for compression molding, such as those temperatures described above. This temperature is maintained for a period of time in the range from about 30 minutes to about 90 minutes, preferably about 60 minutes. Such a melt-soak stage may allow much of, or most of, the mass of the puck to reach about the same temperature. It is further appreciated that additional melt-soak stages at various temperatures may be added as additional steps in variations of the process.

The molding process may involve pressures from about 1,000 psi to about 15,000 psi, preferably pressures from about 1,000 psi to about 9,000 psi, or pressures from about 2,000 psi to about 8,000 psi. The molding process may be optionally performed under vacuum or in an inert or substantially oxygen free atmosphere. It will be appreciated, however, that acceptable results may be achieved for certain bearing configurations when the molding process is carried out under atmospheric conditions, i.e., with some oxygen present.

The molding process may include exerting a small initial pressure on the preform prior to the application of heat. Such an initial pressure is illustratively less than about 1,000 psi, and preferably in the range from about 50 psi to about 250 psi. It is appreciated that when higher temperatures are used to perform the compression molding that a lower initial pressure may be exerted on the preform. Alternatively, it is further appreciated that when lower temperatures are used to perform the compression molding that higher initial pressures may be exerted on the preform.

The molding process may also include a second pressurization that follows the application of heat, illustratively during a melt-soak stage. Such a second pressurization is illustratively less than about 1,000 psi, and preferably in the range from about 150 psi to about 800 psi. It is appreciated that when higher temperatures are used in the melt-soak stage that a lower initial pressure may be exerted on the preform. Alternatively, it is further appreciated that when lower temperatures are used in the melt-soak stage that higher initial pressures may be exerted on the preform.

It is appreciated that additional pressurization steps or stages of pressurization may be added to the process. Such additional steps or stages may be desirable for certain bearing configurations.

The final molded bearing dimensions resulting from the compression molding process are such that the cross-sectional area of the bearing, in a plane transverse to the compression direction, is greater than the cross-sectional area of the puck or preform used at the outset of the compression molding process. Furthermore, the compression molding process of the present invention is embodied as a low compression-ratio molding process, as characterized by the flow ratio. The term "flow ratio" is defined herein as the ratio of the final bearing radius to the preform radius. For bearings and preforms that are not substantially circular or elliptical, another measurement such as length or width may be used to determine the flow ratio. Low compression-ratio processes involve a flow ratio that is typically less than 2, illustratively from about 1.05 to about 1.7, or preferably from about 1.1 to about 1.3, or more preferably from about 1.2 to about 1.3.

Following compression molding, the pressure exerted by the molding press on the formed bearing will be maintained during cooling of the bearing. It is appreciated that maintaining the pressure on the molded bearing while cooling will discourage the relaxation of the polyethylene back to an unoriented state. Cooling rates may be moderate from about 1° C. per minute or greater, or rapid from about 15° C. per minute or greater. It is appreciated that cooling rates slower than 1° C. per minute or less may be appropriate for certain end-use dependent configurations, particularly configurations requiring crystal orientation. Slower cooling rates tend to increase the degree of crystallinity of the polyethylene observed in the molded bearing. The development of such microcrystalline structures in the molded bearings may also be oriented in a manner analogous to the biaxial molecular orientation, as described above.

In variations of the process, a "recrystallization-soak stage" is inserted into the process following the compression molding. The term "recrystallization-soak stage" as used herein refers to a cooling procedure where the molded bearing, while under pressure, is cooled to, and held at, a temperature above ambient temperature for a period of time without the release of pressure. It is appreciated that including a recrystallization-soak stage may promote the formation of additional crystalline morphology in the molded bearing. Such additional crystalline morphology may discourage the relaxation of the polyethylene back to an unoriented state. Illustratively, the molded bearing may be cooled to an intermediate temperature in the range of about 120° C. to about 160° C., or preferably a temperature in the range of about 130° C. to about 150° C. An illustrative period of time for the recrystallization-soak stage is in the range from about 30 minutes to 60 minutes, or preferably in the range from about 30 minutes to 40 minutes. It is further appreciated that longer periods of time may be used in recrystallization-soak stages performed at higher temperatures, and conversely, shorter periods of time may be used in recrystallization-soak stages performed at lower temperatures. It is appreciated that additional temperature stages or steps added to the process may be desirable for certain bearing configurations.

The actual radiation dose and the compression molding conditions may be chosen to thus obtain a balance from which the wear characteristics of the formed bearing may be obtained by routine optimization. Certain end-use dependent bearing configurations, such as differences in the desired configurations of hip bearings in comparison to those configurations desired for shoulder bearings, may require adjustment of the balance of orientation induction obtained from the compression molding process and the level of cross-linking obtained from the irradiation process. Such adjustment may be achieved by routine experimentation by those of ordinary skill in the art. It is appreciated that various levels of cross-linking and orientation present in the molded bearing, net-shape bearing, or near net-shape bearing may be desirable.

The present invention further pertains to an oriented UHMWPE material prepared by the processes of the present invention. Such oriented polyethylene possesses biaxial orientation, and preferably radially-disposed biaxial molecular orientation in the planes of the material transverse to the compression direction. This compression-induced orientation imparts improved physical properties to UHMWPE. Particularly, oriented UHMWPE and the corresponding molded bearings prepared according to processes described herein exhibit a percent elongation to break of about 250% or greater, and preferably of about 350% or greater, in the compression direction. In addition, oriented UHME prepared according to processes described herein may exhibit a higher tensile strength in the transverse plane, and a greater impact strength in the compression direction, relative to UHMWPE prepared by conventional means. Furthermore, the bearings of the present invention may demonstrate improved wear rates and improved resistance to oxidation.

The tensile strength of the oriented polyethylene can be determined by techniques known to those of ordinary skill in the art, such as according to the ASTM D638 test procedure using 400-μm thick type "V" test specimens, or according to any other test procedure of a similar nature which is commonly practiced or otherwise accepted in the art. The impact strength of the polyethylene can be determined by techniques known to those of ordinary skill in the art, such as using the Double-notched IZOD Impact test based on the ASTM F648 test procedure, or according to any other test procedure of a similar nature which is commonly practiced or otherwise accepted in the art. The oxidation resistance of the polyethylene can be assessed in terms of an Oxidation Index (OI) using Fourier-Transform infrared spectroscopy (FT-IR), or according to any other test procedure of a similar nature which is commonly practiced or otherwise accepted in the art. The OI can be measured for in-process oxidation potential as well as post-process accelerated aging oxidation potential. The protocol for such a post-process accelerated aging procedure may include placing the specimen in an oxygen chamber which is maintained at 70° C. at 5 atm of pressure for two weeks. Alternatively, the oxidation resistance of the polyethylene can be assessed by measuring the oxidative onset temperature. A higher observed value for the measured oxidative onset temperature for a polyethylene reflects a polyethylene with a greater resistance to oxidation.

A more complete understanding of the present invention can be obtained by referring to the following illustrative examples of the practice of the invention. The examples are intended to illustrate the scope and spirit of the invention by way of describing particular embodiments and are not intended, however, to be unduly limiting of the invention.

EXAMPLES

Pucks of undersized diameter relative to the mold diameter were prepared from commercial ram extruded GUR 1020 bar stock. The pucks were irradiated with doses in the range of about 5 Mrad to about 10 Mrad of gamma irradiation in an oxygen-reduced atmosphere using standard procedures. Pucks of cross-linked UHMWPE, optionally stabilized by a melt annealing process are also commercially available. The pre-irradiated samples were centralized in the mold cavity of a standard compression molding apparatus and compression molded with various processing parameters allowing for planar melt flow to achieve mold filling. Orientation was induced after the melt soak stage during compression molding and maintained during the recrystallization and the cooling stages.

Example 1

Oriented Cross-Linked UHMWPE Molded at 2000 psi

A puck of commercially available cross-linked UHMWPE (~5 Mrad or ~10 Mrad) was centralized in a standard compression molding apparatus adapted for compression molding in an evacuated environment. The apparatus was evacuated, the compression mold was pressurized to 250 psi, and the mold platen was heated rapidly, over 10–25 minutes, to about 193° C. The pressure was subsequently increased to 800 psi, and the puck was allowed to reach thermal equilibrium over 60 minutes. Compression molding took place at 2000 psi. The temperature was decreased to 138° C., and the molded article was allowed to reach thermal equilibrium over 30 minutes. Finally, the molded article was allowed to cool to ambient temperature. The 2000 psi pressure was maintained throughout both steps of the cooling procedure.

Example 2

Oriented Cross-Linked UHMWPE Molded at 8000 psi

A puck of commercially available cross-linked UHMWPE (~5 Mrad or ~10 Mrad) was centralized in a standard compression molding apparatus adapted for compression molding in an evacuated environment. The apparatus was evacuated, the compression mold was pressurized to 50 psi, and the mold platen was heated rapidly, over 10–25 minutes, to about 216° C. The pressure was subsequently increased to 150 psi, and the puck was allowed to reach thermal equilibrium over 60 minutes. Compression molding took place at 8000 psi. The temperature was decreased to 149° C., and the molded article was allowed to reach thermal equilibrium over 40 minutes. Finally, the molded article was allowed to cool to ambient temperature. The 8000 psi pressure was maintained throughout both steps of the cooling procedure.

Example 3

Anisotropic Behavior of Oriented Cross-Linked UHMWPE

A sample of oriented cross-linked UHMWPE (10.6 Mrad, 1.40 flow ratio) was heated from ambient temperature to about 190° C. using a TA Instruments 2940 Thermal Mechanical Tester. Thermal expansion and contraction data were generated. The dimensions of the sample were monitored as a function of temperature. A significant relaxation and contraction of the oriented polyethylene chains was observed when the temperature of the sample reached between 134° C. and 141° C. The dimensions of the sample contracted by 1.4%, but only in the plane transverse to the direction of compression, namely the transverse plane. In contrast, over the same temperature range, thermal expansion typical of isotropic UHMWPE was observed in the dimension parallel with the compression direction. The thermally-induced contraction of the compression plane was irreversible, being retained after complete cooling of the sample. Such thermal behavior is indicative of biaxial orientation of the UHMWPE in the transverse plane.

Example 4

Free Radical Quenching During Compression Molding and Oxidation Resistance of Oriented Cross-Linked UHMWPE Compared to Other Samples of UHMWPE Freshly-irradiated UHMWPE (10.6 Mrad) was compression molded (1.40 flow ratio) as described above to induce orientation. The residual free radical concentration in the oriented cross-linked UHMWPE was determined and compared to conventionally prepared UHMWPE (10.6 Mrad, quenched by heat treatment), freshly-irradiated unquenched UHMWPE (10.6 Mrad), and non-cross-linked (raw) UHMWPE. The residual free radical concentration in these samples was determined by measuring peak-to-peak height of electron paramagnetic resonance (EPR) signals. The data are shown in Table I. In addition, post-accelerated aging oxidation was measured in terms of an Oxidation Index (OI) using Fourier-Transform infrared spectroscopy (FT-IR) for each of the samples. These data are also shown in Table I. Finally, the oxidative onset temperature was determined for each of the samples and each is shown in Table I.

The data in Table I show that compression molding to induce orientation in cross-linked UHMWPE also provided substantial quenching of the residual free radical population. Free radical levels were reduced by more than 99% from the level measured in freshly-irradiated unquenched UHMWPE and were comparable to the level found in non-cross-linked UHMWPE.

The data in Table I also show that the oxidation resistance, as assessed by OI, of oriented cross-linked UHMWPE prepared as above, was comparable to that measured for non-cross-linked UHMWPE and UHMWPE cross-linked and quenched with conventional methods. Finally, the data in Table I show that the oxidative onset temperature for the oriented cross-linked UHMWPE was higher than that for either conventionally cross-linked UHMWPE (quenched by heat treatment) or non-cross-linked UHMWPE. Freshly-irradiated UHMWPE had a relatively low oxidative onset temperature.

TABLE I

Oxidation resistance of oriented UHMWPE, conventional cross-linked UHMWPE, irradiated UHMWPE, and non-irradiated UHMWPE, as assessed by EPR, OI, and oxidative onset temperature.

| Sample | Relative EPR Signal | OI (Accelerated Aging) | Oxidative Onset Temperature (° C.) |
|---|---|---|---|
| Oriented | 1.0 | 0.015 | 168.9 |
| Conventional | 1.2 | 0.004 | 168.3 |
| Irradiated & Unquenched | 190 | 0.316 | 165.4 |
| Non-cross-linked | 1.0 | 0.041 | 166.4 |

Example 6

Mechanical Properties of Oriented Cross-Linked UHMWPE Compared to Conventional Cross-Linked UHMWPE The physical properties of the resulting compression molded samples of oriented cross-linked UHMWPE, prepared as above, were evaluated and compared to conventional cross-linked UHMWPE and non-irradiated UHMWPE. The ultimate tensile strength was determined according to the ASTM D638 test procedure using 400-$\mu$m thick type "V" test specimens. The Double-notched IZOD Impact Strength test was performed based on the ASTM F648 test procedure. In addition, fracture energy to break and percent elongation to break were determined using standard test protocols.

The data in Table II and Table III show an improvement in the mechanical properties of the oriented cross-linked UHMWPE prepared in accordance with the present invention when compared to cross-linked UHMWPE prepared with conventional methods. In addition, these data suggest that improvements in tensile strength, impact strength, toughness, and percent elongation to break are directionally-dependent. The tensile strength was improved in the transverse plane in the oriented cross-linked UHMWPE, without any loss of tensile strength in the compression direction, when compared to conventionally prepared cross-linked UHMWPE. The percent elongation to break and the impact strength were both improved in the compression direction, without a significant loss of these two mechanical properties in the transverse plane, when compared to conventionally prepared cross-linked UHMWPE. Finally, the toughness, namely the measured energy required to achieve tensile fracture, trends toward an improvement in the compression direction for the oriented cross-linked UHMWPE, when compared to conventionally prepared cross-linked UHMWPE.

TABLE II

Mechanical properties of oriented cross-linked UHMWPE (5.4 Mrad) in two directions and conventional cross-linked UHMWPE (5 Mrad).

| Sample | Flow Ratio | Ultimate Tensile Strength (ksi) | Elongation to Break (%) | Fracture Energy at Break (ksi) | Double Notched Izod Impact Strength (KJ/m$^2$) |
|---|---|---|---|---|---|
| Oriented (transverse plane) | 1.06 | 8.49 ± 0.43 | 280 ± 33 | 12.9 ± 1.7 | 76 ± 2 |
| Oriented (compression direction) | 1.06 | 7.10 ± 0.47 | 332 ± 27 | 12.6 ± 1.3 | 81 ± 5 |
| Oriented (transverse plane) | 1.12 | 8.10 ± 0.47 | 283 ± 18 | 12.6 ± 1.1 | 78 ± 1 |
| Oriented (compression direction) | 1.12 | 6.87 ± 0.23 | 435 ± 25 | 15.1 ± 1.2 | 94 ± 8 |
| Oriented (transverse plane) | 1.20 | 8.67 ± 0.66 | 280 ± 24 | 13.1 ± 1.6 | 74 ± 2 |
| Oriented (compression direction) | 1.20 | 6.47 ± 0.39 | 474 ± 78 | 15.8 ± 1.9 | 110 ± 13 |
| Conventional | — | 6.84 ± 0.99 | 308 ± 38 | 10.4 ± 1.9 | 71 ± 1 |

TABLE III

Mechanical properties of oriented cross-linked UHMWPE (10.6 Mrad) in two directions and conventional cross-linked UHMWPE (10.6 Mrad).

| Sample | Flow Ratio | Ultimate Tensile Strength (ksi) | Elongation to Break (%) | Fracture Energy at Break (ksi) | Double Notched Izod Impact Strength (KJ/m$^2$) |
|---|---|---|---|---|---|
| Oriented (transverse plane) | 1.40 | 8.3 | 298 | 11.2 | 91 |
| Oriented (compression direction) | 1.40 | 7.0 | 412 | 12.2 | 62 |
| Conventional | — | 6.5 | 294 | 9.4 | 73 |

Example 7
Wear Test Data for Various UHMWPE Samples Measured by Pin-on-Disk

Several samples of UHMWPE, oriented cross-linked UHMWPE (various flow ratios), conventional UHMWPE (cross-linked and quenched by heat treatment), freshly-irradiated and unquenched UHMWPE, and non-cross-linked (raw) UHMWPE, were subjected to wear tests using the standard Pin-on-Disk test protocol. All cross-linked or irradiated samples of UHMWPE were treated with a dose of about 5.4 Mrad to about 5.6 Mrad of gamma irradiation. The data in Table IV show that the oriented cross-linked UHMWPE demonstrated a comparable wear rate to that observed for conventional UHMWPE, and a lower wear rate than that observed for either irradiated and unquenched UHMWPE, or non-cross-linked UHMWPE.

TABLE IV

Pin-on-Disk wear data for various UHMWPE samples.

| Sample | Flow Ratio | Wear Rate (mg/million cycles) |
|---|---|---|
| Oriented (compression direction) | 1.12 | 4.83 ± 0.68 |
| Oriented (transverse plane) | 1.40 | 4.71 ± 1.88 |
| Oriented (compression direction) | 1.40 | 6.89 ± 1.31 |
| Conventional | — | 5.65 ± 0.35 |
| Irradiated & Unquenched | — | 12.29 ± 0.78 |
| Non-cross-linked | — | 17.58 ± 0.34 |

While the invention has been illustrated and described in detail in the drawings and foregoing description, such an illustration and description is to be considered as exemplary and not restrictive in character, it being understood that only the illustrative embodiments have been shown and described and that all changes and modifications that come within the spirit of the invention are desired to be protected.

There are a plurality of advantages of the present invention arising from the various features of the prosthetic bearing described herein. It will be noted that alternative embodiments of each of the prosthetic bearings of the present invention may not include all of the features described yet still benefit from at least some of the advantages of such features. Those of ordinary skill in the art may readily devise their own implementations of a prosthetic bearing that incorporate one or more of the features of the present invention and fall within the spirit and scope of the present invention as defined by the appended claims.

For example, although it has been described herein to cross-link materials via irradiation, a process which has numerous advantages in regard to the present invention, it should be appreciated that certain of such advantages may be achieved by cross-linking the materials by any other suitable technique.

What is claimed is:

1. A process for preparing an orthopaedic bearing, comprising the steps of:
    irradiating an ultrahigh molecular weight polyethylene preform with a dose of gamma radiation within a range from about 5.1 Mrad to about 50 Mrad;
    placing the preform in a compression molding press;
    heating the preform to a temperature that is greater than or substantially equal to the melting temperature of the ultrahigh molecular weight polyethylene; and
    compression molding the preform under a pressure effective to orient the ultrahigh molecular weight polyethylene outwardly from the direction of compression to form the bearing.

2. The process of claim 1, further comprising the step of cooling the bearing while maintaining the bearing under pressure.

3. The process of claim 1, wherein the irradiating step includes irradiating the preform with a dose of gamma radiation within the range from about 5.1 Mrad to about 15 Mrad.

4. The process of claim 1, wherein the compression molding step is effective to induce planar flow in the preform.

5. The process of claim 1, wherein the compression molding step is effective to induce biaxial orientation of the ultrahigh molecular weight polyethylene in a number of planes which are transverse to a compression direction.

6. The process of claim 1, wherein the compression molding step is effective to induce biaxial molecular orientation of the ultrahigh molecular weight polyethylene in a number of planes which are transverse to a compression direction.

7. The process of claim 1, wherein the compression molding step is effective to induce radially-disposed molecular orientation of the ultrahigh molecular weight polyethylene in a number of planes which are transverse to a compression direction.

8. The process of claim 1, wherein the compression molding step is effective to quench a population of residual free radicals present in the preform.

9. The process of claim 1, wherein the compression molding step is effective to reduce a population of residual free radicals by about 90% or greater.

10. The process of claim 1, wherein the compression molding step is effective to reduce a population of residual free radicals by about 95% or greater.

11. The process of claim 1, wherein the compression molding step includes compressing the preform to form the bearing to a flow ratio within a range of 1.05 to about 1.7.

12. The process of claim 1, wherein the compression molding step includes compressing the preform to form the bearing to a flow ratio within a range of 1.1 to about 1.3.

13. The process of claim 1, wherein the compression molding step includes compressing the preform to form the bearing to a flow ratio within a range of 1.1 to about 1.2.

14. The process of claim 2, wherein the cooling step is performed while the bearing is in the mold.

15. A process for preparing an oriented polyethylene orthopaedic bearing, comprising the steps of:
    placing an irradiated polyethylene preform into a compression molding press; and
    compression molding the preform so as to form the bearing by compressive forces effective to (i) orient the polyethylene outwardly from the direction of compression, and (ii) form the bearing at a flow ratio within a range of 1.1 to 1.3.

16. The process of claim 15, wherein:
    the irradiated polyethylene preform includes an irradiated ultrahigh molecular weight polyethylene preform, and
    the placing step includes placing the irradiated ultrahigh molecular weight polyethylene preform into the compression molding press.

17. The process of claim 15, further comprising the step of heating the preform.

18. The process of claim 17, wherein the heating step is performed prior to the compression molding step.

19. The process of claim 17, wherein the heating step is performed contemporaneously with the compression molding step.

20. The process of claim 17, wherein the heating step includes heating the preform to a temperature above the melting temperature of the polyethylene.

21. The process of claim 17, wherein the compression molding step is performed in a substantially oxygen-free atmosphere.

22. A process for preparing an oriented polyethylene orthopaedic net-shape bearing, comprising the steps of:
placing an irradiated polyethylene preform into a compression molding press; and
compression molding the preform so as to form the net-shape bearing by compressive forces effective to orient the polyethylene outwardly from the direction of compression.

23. The process of claim 22, wherein:
the irradiated polyethylene preform includes an irradiated ultrahigh molecular weight polyethylene preform, and
the placing step includes placing the irradiated ultrahigh molecular weight polyethylene preform into the compression molding press.

24. The process of claim 22, further comprising the step of heating the preform.

25. The process of claim 24, wherein the heating step is performed prior to the compression molding step.

26. The process of claim 24, wherein the heating step is performed contemporaneously with the compression molding step.

27. The process of claim 24, wherein the heating step includes heating the preform to a temperature above the melting temperature of the polyethylene.

28. The process of claim 22, wherein the compression molding step includes compressing the preform under a pressure within the range from about 1,000 psi to about 15,000 psi.

29. The process of claim 22, wherein the compression molding step includes compressing the preform to form of the net-shape bearing at a flow ratio within the range of 1.1 to 1.3.

30. The process of claim 22, wherein the compression molding step is performed in a substantially oxygen-free atmosphere.

31. A process for preparing an oriented polyethylene orthopaedic bearing, comprising the steps of:
placing a polyethylene preform, which has been irradiated with a dose of gamma radiation within a range from about 5.1 Mrad to about 50 Mrad, into a compression molding press; and
compression molding the preform so as to form the bearing by compressive forces effective to orient the polyethylene outwardly from the direction of compression.

32. The process of claim 31, wherein:
the polyethylene preform includes an ultrahigh molecular weight polyethylene preform, and
the placing step includes placing the ultrahigh molecular weight polyethylene preform into the compression molding press.

33. The process of claim 31, further comprising the step of heating the preform.

34. The process of claim 33, wherein the heating step includes heating the preform to a temperature above the melting temperature of the polyethylene.

35. The process of claim 31, wherein the compression molding step includes compressing the preform to form the bearing to a flow ratio within a range of 1.1 to about 1.3.

36. The process of claim 15, further comprising the step of cooling the bearing while maintaining the bearing under pressure.

37. The process of claim 2, further comprising the step of cooling the bearing while maintaining the bearing under pressure.

38. The process of claim 31, further comprising the step of cooling the bearing while maintaining the bearing under pressure.

39. The process of claim 1, further comprising the step of preheating the preform prior to the placing step.

40. The process of claim 15, further comprising the step of preheating the preform prior to the placing step.

41. The process of claim 22, further comprising the step of preheating the preform prior to the placing step.

42. The process of claim 31, further comprising the step of preheating the preform prior to the placing step.

43. The process of claim 1, further comprising the step of soaking the preform for a period of time at a soak pressure which is less than the pressure generated by the pressure effective to orient the ultrahigh molecular weight polyethylene, wherein the soaking step is performed after the heating step.

44. The process of claim 17, further comprising the step of soaking the preform for a period of time at a soak pressure which is less than the pressure generated by the compressive forces, wherein the soaking step is performed after the heating step.

45. The process of claim 24, further comprising the step of soaking the preform for a period of time at a soak pressure which is less than the pressure generated by the compressive forces, wherein the soaking step is performed after the heating step.

46. The process of claim 33, further comprising the step of soaking the preform for a period of time at a soak pressure which is less than the pressure generated by the compressive forces, wherein the soaking step is performed after the heating step.

47. The process of claim 1, further comprising the step of exerting an initial pressure on the preform prior to the heating step, wherein the initial pressure is less than the pressure generated by the pressure effective to orient the ultrahigh molecular weight polyethylene.

48. The process of claim 1, further comprising the step of exerting an intermediate pressure on the preform subsequent to the heating step, wherein the intermediate pressure is less than the pressure generated by the pressure effective to orient the ultrahigh molecular weight polyethylene.

49. The process of claim 17, further comprising the step of exerting an initial pressure on the preform prior to the heating step, wherein the initial pressure is less than the pressure generated by the compressive forces.

50. The process of claim 17, further comprising the step of exerting an intermediate pressure on the preform subsequent to the heating step, wherein the intermediate pressure is less than the pressure generated by the compressive forces.

51. The process of claim 24, further comprising the step of exerting an initial pressure on the preform prior to the heating step, wherein the initial pressure is less than the pressure generated by the compressive forces.

52. The process of claim 24, further comprising the step of exerting an intermediate pressure on the preform subsequent to the heating step, wherein the intermediate pressure is less than the pressure generated by the compressive forces.

53. The process of claim 33, further comprising the step of exerting an initial pressure on the preform prior to the heating step, wherein the initial pressure is less than the pressure generated by the compressive forces.

54. The process of claim 33, further comprising the step of exerting an intermediate pressure on the preform subsequent to the heating step, wherein the intermediate pressure is less than the pressure generated by the compressive forces.

55. The process of claim 1, further comprising the step of soaking the bearing for a period of time, after the compression molding step, at a temperature which is greater than ambient temperature, wherein the bearing is maintained under pressure during the soaking step.

56. The process of claim 15, further comprising the step of soaking the bearing for a period of time, after the compression molding step, at a temperature which is greater than ambient temperature, wherein the bearing is maintained under pressure during the soaking step.

57. The process of claim 22, further comprising the step of soaking the bearing for a period of time, after the compression molding step, at a temperature which is greater than ambient temperature, wherein the bearing is maintained under pressure during the soak step.

58. The process of claim 31, further comprising the step of soaking the bearing for a period of time, after the compression molding step, at a temperature which is greater than ambient temperature, wherein the bearing is maintained under pressure during the soaking step.

59. The process of claim 1, further comprising the step of quenching the preform prior to the compression molding step.

60. The process of claim 15, further comprising the step of quenching the preform prior to the compression molding step.

61. The process of claim 22, further comprising the step of quenching the preform prior to the compression molding step.

62. The process of claim 31, further comprising the step of quenching the preform prior to the compression molding step.

* * * * *